United States Patent
McKay et al.

(10) Patent No.: US 9,023,023 B2
(45) Date of Patent: *May 5, 2015

(54) NERVE AND SOFT TISSUE ABLATION DEVICE

(71) Applicant: Warsaw Orthopedic, Inc., Warsaw, IN (US)

(72) Inventors: William F. McKay, Memphis, TN (US); Josee Roy, Memphis, TN (US)

(73) Assignee: Warsaw Orthopedic, Inc., Warsaw, IN (US)

(*) Notice: Subject to any disclaimer, the term of this patent is extended or adjusted under 35 U.S.C. 154(b) by 179 days.

This patent is subject to a terminal disclaimer.

(21) Appl. No.: 13/835,155

(22) Filed: Mar. 15, 2013

(65) Prior Publication Data

US 2014/0276700 A1    Sep. 18, 2014

(51) Int. Cl.
*A61B 18/18* (2006.01)
*A61B 18/02* (2006.01)
*A61B 18/00* (2006.01)

(52) U.S. Cl.
CPC ............ *A61B 18/0218* (2013.01); *A61B 18/02* (2013.01); *A61B 2018/00434* (2013.01); *A61B 2018/0044* (2013.01); *A61B 2018/0262* (2013.01); *A61B 2018/0293* (2013.01); *A61B 2218/002* (2013.01)

(58) Field of Classification Search
CPC .................................................. A61B 18/2018
USPC .......................................................... 606/23
See application file for complete search history.

(56) References Cited

U.S. PATENT DOCUMENTS

| 5,147,355 | A | | 9/1992 | Friedman et al. |
|---|---|---|---|---|
| 5,334,181 | A | | 8/1994 | Rubinsky et al. |
| 5,520,682 | A | | 5/1996 | Baust et al. |
| 5,906,612 | A | * | 5/1999 | Chinn ........................ 606/20 |
| 6,032,675 | A | | 3/2000 | Rubinsky |
| 6,179,831 | B1 | | 1/2001 | Bliweis |
| 6,190,378 | B1 | | 2/2001 | Jarvinen |
| 6,485,422 | B1 | | 11/2002 | Mikus et al. |
| 6,579,287 | B2 | | 6/2003 | Wittenberger et al. |
| 6,672,095 | B1 | | 1/2004 | Luo |
| 6,761,715 | B2 | | 7/2004 | Carroll |
| 6,789,545 | B2 | | 9/2004 | Littrup et al. |
| 6,796,979 | B2 | | 9/2004 | Lentz |
| 6,902,547 | B2 | | 6/2005 | Aves et al. |
| 6,926,711 | B2 | | 8/2005 | Lentz et al. |

(Continued)

FOREIGN PATENT DOCUMENTS

WO    2010102310 A2    9/2010

*Primary Examiner* — Robert N Wieland (57) ABSTRACT

Ablation devices useful for removing nerve and soft tissue via a minimally invasive procedure to alleviate pain are provided. The device comprises a plurality of probes each comprising an interior surface defining an internal passage and an exterior surface comprising a tip. The internal passage has a filament comprising an opening configured to release a pressurized material into the interior surface of the probe so as to cool the exterior surface of the probe to a selected temperature. A plurality of introducers are provided each comprising an interior surface configured for engagement with the probe where at least one air gap is produced by the introducer and probe engagement and an exterior surface comprising a heat conductive tip where the probe tip is snap fixed with the introducer tip in a configuration for ablating nerve and/or soft tissue. Methods for ablating nerve and/or soft tissue utilizing the ablation devices are also provided.

20 Claims, 4 Drawing Sheets

(56) References Cited

U.S. PATENT DOCUMENTS

| | | |
|---|---|---|
| 7,381,208 B2 | 6/2008 | Van Der Walt et al. |
| 7,510,554 B2 | 3/2009 | Duong et al. |
| 7,625,368 B2 | 12/2009 | Schechter et al. |
| 7,641,679 B2 | 1/2010 | Joye et al. |
| 7,846,154 B2 | 12/2010 | Bliweis et al. |
| 7,938,822 B1 | 5/2011 | Berzak et al. |
| 7,967,814 B2 | 6/2011 | Levin |
| 7,967,815 B1 | 6/2011 | Berzak et al. |
| 8,083,733 B2 | 12/2011 | Toubia et al. |
| 8,162,812 B2 | 4/2012 | Shai et al. |
| 2001/0035189 A1* | 11/2001 | Dobak, III .................... 128/898 |
| 2002/0068964 A1 | 6/2002 | Dobak |
| 2004/0049177 A1 | 3/2004 | Zvuloni et al. |
| 2005/0177215 A1 | 8/2005 | Rosenberg |
| 2005/0240239 A1 | 10/2005 | Boveja et al. |
| 2007/0156125 A1 | 7/2007 | DeLonzor |
| 2007/0191732 A1 | 8/2007 | Voegele |
| 2008/0306475 A1 | 12/2008 | Lentz et al. |
| 2009/0036823 A1 | 2/2009 | LePivert |
| 2009/0192505 A1 | 7/2009 | Askew et al. |
| 2009/0299357 A1 | 12/2009 | Zhou |
| 2010/0168739 A1 | 7/2010 | Wu et al. |
| 2010/0179527 A1 | 7/2010 | Watson et al. |
| 2010/0292764 A1 | 11/2010 | Soomro et al. |
| 2011/0270238 A1 | 11/2011 | Rizq et al. |
| 2011/0313411 A1 | 12/2011 | Anderson et al. |
| 2012/0046531 A1 | 2/2012 | Hua |
| 2012/0065630 A1 | 3/2012 | Berzak et al. |
| 2012/0089047 A1 | 4/2012 | Ryba et al. |
| 2012/0109116 A1 | 5/2012 | Asconeguy et al. |
| 2012/0253336 A1 | 10/2012 | Littrup et al. |
| 2014/0221991 A1* | 8/2014 | Littrup et al. .................. 606/21 |

\* cited by examiner

NERVE AND SOFT TISSUE ABLATION DEVICE

FIELD

The present invention relates generally to devices and methods for ablating a material or substance. More specifically, the devices and methods are useful for removing nerve and/or soft tissue via a minimally invasive procedure to alleviate pain.

BACKGROUND

Acute and chronic pain management has been a concern for as long as medicine has been practiced. Several methods of inducing analgesia and anesthesia have been developed. For example, the use of chemical substances is perhaps the most common approach to pain relief which requires suitable substances that are effective, safe to humans, and do not cause complications or abnormal reactions. Despite the great advances that have been made in the field of anesthesiology, and in the field of pain relief in general, there are still some drawbacks to chemical-based approaches. For instance, the anesthetics generally available today must be administered in carefully graduated doses to assure the patient's well being, require extended periods of fasting prior to treatment, and are often accompanied by undesirable after effects such as nausea.

One alternative approach that is commonly used for providing pain relief is ablation in which nerves and/or tissue is removed and/or destroyed. Two approaches to removing tissue via ablation are through cold or hot ablation procedures and techniques. Various categories of ablation include but are not limited to electrical, radiation, light, radiofrequency, ultrasound, cryotherapy, thermal, microwave and hydromechanical. One form of hot ablation is radiofrequency ablation. During radiofrequency (RF) ablation, current passing through tissue from the active electrode leads to ion agitation, which is converted by means of friction into heat. The process of cellular heating includes almost immediate and irreparable cellular damage, which leads to coagulation necrosis. Because ion agitation, and thus tissue heating, is greatest in areas of highest current density (e.g., closest to the active electrode tip), necrosis is limited to a relatively small volume of tissue surrounding the RF electrode.

Another form of ablation uses cold ablation and is called cryoablation. During cryoablation, tissue is frozen or rapid freeze/thaw cycles are inflicted upon the tissue. There are many advantages to using cryoablation instead of radiofrequency ablation. For example, cryoablation is safer especially near critical vasculature and there is less risk of post-procedure neuritis or neuromas following neuroablation for the treatment of pain. Cryoablation allows treatment mapping pre and post procedure where areas of tissue can be mapped by limited, reversible and/or freezing. Cryoablation can be monitored and visualized on ultrasonography, CT and MRI. Moreover, because nerve cooling is anesthetic, cryoablation is a less painful procedure than thermal ablation techniques.

The current procedures and techniques using cryoablation used destroy tissue due to rupturing of cells and/or cell organelles within the tissue. Deep tissue freezing is affected by insertion of a tip of a cryosurgical device into the tissue, either transperineally, endoscopically or laproscopically, and a formation of, what is known in the art as, an ice ball around the tip. During freezing, ice formation within the extracellular space creates an osmotic gradient, resulting in cellular dehydration. Ice crystals then form within the cells causing cell membranes to rupture resulting in cell death.

In addition, when the adjacent tissues are present at opposite borders with respect to the freeze treated tissue and since the growth of the ice ball is in a substantially similar rate in all directions toward its periphery, if otherwise, the ice ball reaches one of the borders before it reaches the other border, and decision making must be made on whether to continue the process of freezing, risking damage to close healthy tissues, or to halt the process of freezing, risking a non-complete destruction of the treated tissue.

Traditional cryoablation systems can provide destruction capabilities of soft tissue via the application of single needles that form an ice ball centered around a tip, but the procedures can take a considerable amount of time to perform because the ice balls are directly attached to the needle tips and a medical practitioner must wait for the ice balls to melt enough in order to remove the needles from the site.

Another problem with currently available cryoablation devices is that they are not cost effective. The needles used during a procedure are disposed of after use and are not reusable. Further, if a single needle is used for a procedure, contamination of the surgical site can occur.

Further, the health care practitioner may have difficulty positioning the tip of the device in the optimal location to get an optimal and consistent clinical result. This may also result in unwanted necrosis of adjacent tissue, which can lead to clinical adverse events including subsequent repair of the necrotic tissue.

Accordingly, there is a need for devices and methods to provide efficient destruction of nerve and/or soft tissue ablation by utilizing a device that allows a medical practitioner to position the components of the device at various locations, such as, for example, multiple facet joints and/or multiple spinal levels such that the medical practitioner can quickly move the device from one location to the next without waiting for an extended period of time for ice ball melting to remove the device from the site. Moreover, a device is needed for use during a minimally invasive procedure and/or during an open surgical procedure. Further, there is a need for devices and methods that provide fine ablation capabilities of nerve and/or soft tissue. Devices and methods that assist in the control of necrosis in a tissue being treated are also needed.

SUMMARY

Ablation devices and methods are provided that shorten the length of a procedure and reduce the costs of the procedure. The ablation devices and methods provided allow the tips of the device to be easily positioned in an optimal location to obtain improved ablation with minimal unwanted destruction to adjacent nerve and/or soft tissue. The devices and methods provided are reusable for multiple procedures and are antimicrobial.

In some embodiments, the ablation devices and methods provided allow destruction of nerves and other soft tissue via a minimally invasive procedure to alleviate pain. The ablation devices and methods disclosed comprise a plurality of probes where each probe comprises an interior surface defining an internal passage and an exterior surface comprising a tip. The internal passage has a filament comprising an opening configured to release a pressurized material (i.e. argon, liquid nitrogen) into the interior surface of the probe so as to cool the exterior surface of the probe to a selected temperature. The device includes a plurality of introducers where each introducer comprises an interior surface configured for engagement with the probe. At least one air gap is produced by the introducer and probe engagement. Each introducer includes an exterior surface comprising a heat conductive tip and the probe tip is placed in direct contact with the introducer tip in a configuration for ablating nerve and/or soft tissue.

In some embodiments, a cryoablation device comprises a probe comprising an interior surface that defines an internal passage and an exterior surface comprising a tip. The internal passage has a filament comprising an opening configured to release a pressurized material into the interior surface of the probe so as to cool the exterior surface of the probe to a selected temperature. The device comprises a plurality of sleeves each comprising an interior surface configured for disposal of the probe and an exterior surface comprising an opening. The tip of the probe extends from the exterior surface opening to ablate nerve and/or soft tissue at a facet or sacroiliac joint.

In certain embodiments, methods for destroying nerves and other soft tissue via a minimally invasive procedure to alleviate pain are also provided. Destruction of the target nerve or soft tissue can eliminate and/or reduce pain symptoms. Specific clinical applications of the disclosed ablation instrument include destruction of nerves causing facet and discogenic back and leg pain, destruction of soft tissue causing stenosis pain symptoms, and many other orthopedic, oral maxillofacial and ENT pains and pathologies.

In some embodiments, methods of ablating a nerve and/or soft tissue include disposing a plurality of introducers at a surgical site; inserting a plurality of probes within a plurality of introducers, wherein each probe comprises an interior surface defining an internal passage and an exterior surface comprising a tip, wherein the internal passage has a filament comprising an opening configured to release a pressurized material into the interior surface of the probe so as to cool the exterior surface of the probe to a selected temperature and wherein each introducer comprises an interior surface configured for engagement with the probe, wherein at least one air gap is produced by the introducer and probe engagement, and an exterior surface comprising a heat conductive tip, wherein the probe tip is placed in contact with the introducer tip in a configuration for ablating nerve and/or soft tissue; and placing the device adjacent to the nerve and/or soft tissue to ablate the nerve and/or soft tissue.

In some embodiments, there is a method of ablating a nerve and/or soft tissue, comprising: inserting a plurality of introducers at a surgical site; inserting a probe within a first of the plurality of introducers, wherein the probe comprises an interior surface defining an internal passage and an exterior surface comprising a tip, the internal passage having a filament comprising an opening configured to release a pressurized material into the interior surface of the probe so as to cool the exterior surface of the probe to a selected temperature to ablate the nerve and/or soft tissue; and removing the probe from the first of the plurality of introducers and inserting the probe into a second of the plurality of introducers to ablate the nerve and/or soft tissue adjacent to the introducer and/or probe.

Additional features and advantages of various embodiments will be set forth in part in the description that follows, and in part will be apparent from the description, or may be learned by practice of various embodiments. The objectives and other advantages of various embodiments will be realized and attained by means of the elements and combinations particularly pointed out in the description and appended claims.

BRIEF DESCRIPTION OF THE DRAWINGS

In part, other aspects, features, benefits and advantages of the embodiments will be apparent with regard to the following description, appended claims and accompanying drawings where:

It is to be understood that the figures are not drawn to scale. Further, the relation between objects in a figure may not be to scale, and may in fact have a reverse relationship as to size. The figures are intended to bring understanding and clarity to the structure of each object shown, and thus, some features may be exaggerated in order to illustrate a specific feature of a structure.

DETAILED DESCRIPTION

Devices for efficient destruction and/or removing of a material or substance such as nerve and soft tissue suitable for use in open surgical and/or minimally invasive procedures for the treatment of pain are disclosed. The following description is presented to enable any person skilled in the art to make and use the present disclosure. Descriptions of specific embodiments and applications are provided only as examples and various modifications will be readily apparent to those skilled in the art.

The present disclosure may be understood more readily by reference to the following detailed description of the disclosure presented in connection with the accompanying drawings, which together form a part of this disclosure. It is to be understood that this disclosure is not limited to the specific devices, methods, conditions or parameters described and/or shown herein, and that the terminology used herein is for the purpose of describing particular embodiments by way of example only and is not intended to be limiting of the claimed disclosure.

DEFINITIONS

As used in the specification and including the appended claims, the singular forms "a," "an," and "the" include the plural, and reference to a particular numerical value includes at least that particular value, unless the context clearly dictates otherwise.

Ranges may be expressed herein as from "about" or "approximately" one particular value and/or to "about" or "approximately" another particular value. When such a range is expressed, another embodiment includes from the one particular value and/or to the other particular value.

Similarly, when values are expressed as approximations, by use of the antecedent "about," it will be understood that the particular value forms another embodiment. It is also understood that all spatial references, such as, for example, horizontal, vertical, top, upper, lower, bottom, left and right, are for illustrative purposes only and can be varied within the scope of the disclosure.

For purposes of the description contained herein, with respect to components and movement of components described herein, "forward" or "distal" (and forms thereof) means forward, toward or in the direction of the forward, distal end of the probe portion of the device that is described herein, and "rearward" or "proximal" (and forms thereof) means rearward or away from the direction of the forward, distal end of the probe portion of the device that is described herein. However, it should be understood that these uses of these terms are for purposes of reference and orientation with respect to the description and drawings herein, and are not intended to limit the scope of the claims.

Spatially relative terms such as "under", "below", "lower", "over", "upper", and the like, are used for ease of description to explain the positioning of one element relative to a second element. These terms are intended to encompass different orientations of the device in addition to different orientations than those depicted in the figures. Further, terms such as "first", "second", and the like, are also used to describe various elements, regions, sections, etc. and are also not intended to be limiting. Like terms refer to like elements throughout the description.

As used herein, the terms "having", "containing", "including", "comprising" and the like are open ended terms that indicate the presence of stated elements or features, but do not preclude additional elements or features.

The headings below are not meant to limit the disclosure in any way; embodiments under any one heading may be used in conjunction with embodiments under any other heading.

Reference will now be made in detail to certain embodiments of the invention, examples of which are illustrated in the accompanying drawings. While the invention will be described in conjunction with the illustrated embodiments, it will be understood that they are not intended to limit the invention to those embodiments. On the contrary, the invention is intended to cover all alternatives, modifications, and equivalents that may be included within the invention as defined by the appended claims.

Cryoablation

Cryoablation devices have been available to surgeons to treat many medical conditions, for example, in the treatment of tumors in lung, liver, kidney and other body organs. Cryoablation has also been used for treatment of tumors, cardiac arrhythmias, chronic and post-operative pain, bone fracture and soft tissue wounds.

Cold temperatures have been used to decrease inflammation and to relieve pain since the ancient Egyptians. Liquid air and carbon dioxide were used to treat skin lesions in the beginning of the twentieth century. In 1950, liquid nitrogen was introduced into clinical practice for the cryosurgical ablation of a variety of skin diseases and allowed for deeper tissue to be treated with cryoablation. In 1961, a liquid nitrogen probe was developed and was used to treat Parkinson's disease as well as inoperable brain tumors. From 1980-2000, systems emerged based on an advanced gas expansion method known as the Joule-Thomson Principle. This principle allows for temperature change of a gas or liquid when it is forced through a valve or porous plug while being kept insulated so that no heat is exchanged with the environment. The refrigerant could be stored at room temperature and the difficulties associated with supplying liquid nitrogen to the operating room disappeared. Three main refrigerants were utilized: nitric oxide, liquid nitrogen and argon. For over 20 years, rigid cryoprobes have existed for percutaneous use or in open invasive surgical procedures. For example, cryoprobes are used for freezing a range of lesions from prostate tissue to metastatic cancers in liver. Neuronal tissue has been frozen with such devices for the relief of pain.

Current cryoablation procedures and technique employ cryoprobes that utilize single needles that form an ice ball centered around a tip that are disposed at a surgical site. Before the tip can be positioned into another area of the surgical site, a medical practitioner must wait for the ice ball to adequately melt before removal. Therefore, to ablate multiple areas of the surgical site, a considerable amount of time is wasted and the amount of time that it takes to perform a procedure is lengthened. Furthermore, when a single needle is used for a procedure, contamination of the surgical site can result. Therefore, the probe of the present disclosure decreases the amount of time and contamination that potentially can occur for enhanced ablation.

The present disclosure incorporates at least a single probe or multiple probes and at least a single sleeve or multiple sleeves into a single device that is capable of quickly ablating multiple areas of a surgical site. The use of a single probe and multiple sleeves or multiple probes and multiple sleeves in the present disclosure allows a probe to be quickly removed from a surgical site and/or provides a sterilized environment for a procedure to be executed in.

Figure 1:
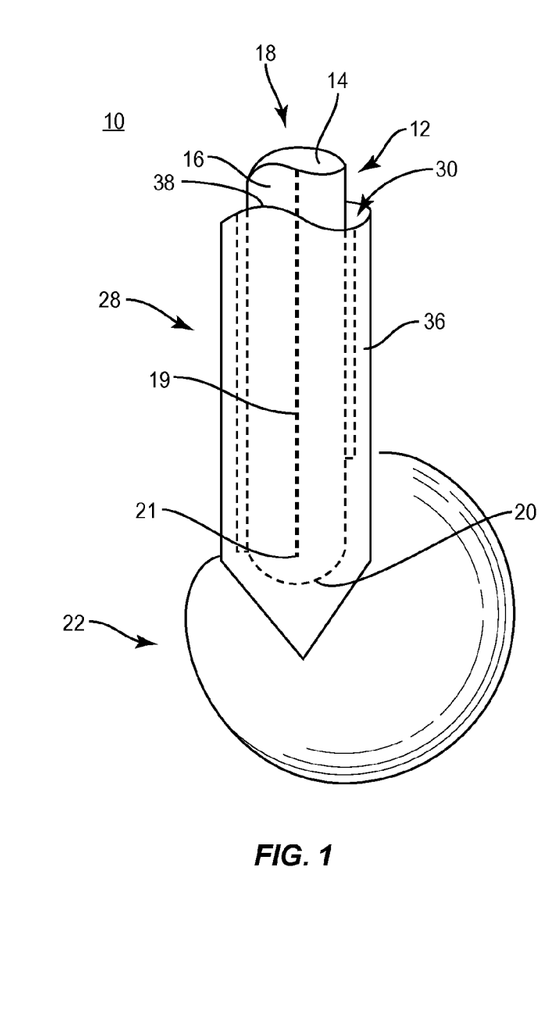
FIG. 1 illustrates a front view of an ablation device in accordance with one embodiment of the present disclosure.
Figure 2:
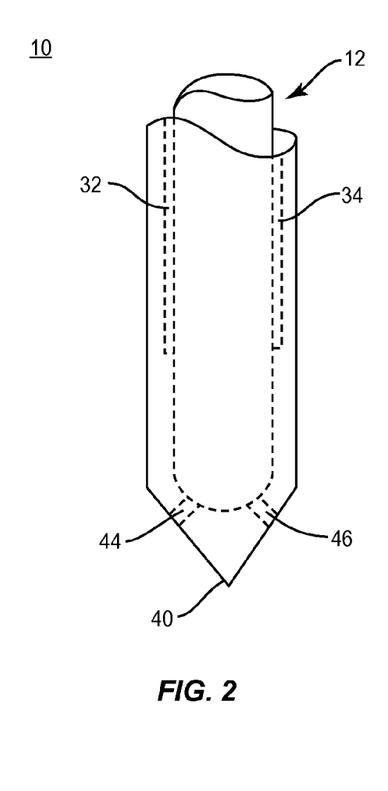
FIG. 2 illustrates a front view of an ablation device in accordance with one embodiment of the present disclosure.
Figure 3:
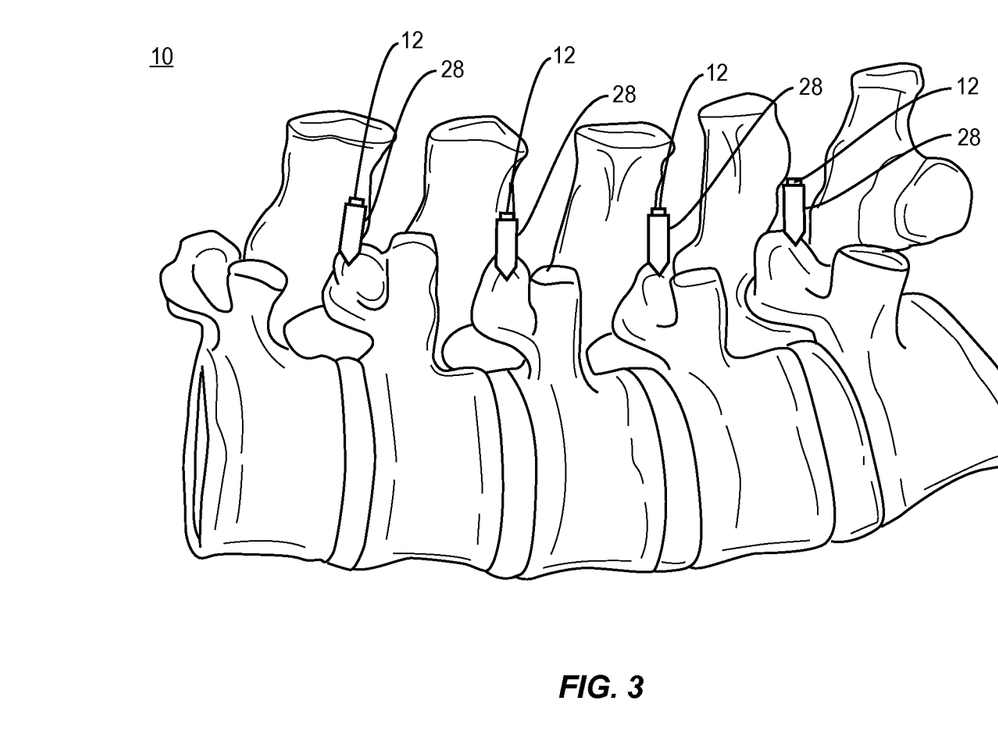
FIG. 3 illustrates a front view of an ablation device in accordance with one embodiment of the present disclosure disposed with vertebrae.

As illustrated in FIGS. 1-7, the present ablation device 10 comprises a plurality of probes, such as, for example, a probe 12 (FIGS. 1-2). In various embodiments, device 10 includes at least four probes (FIG. 3). The dimensions of the device, among other things, will depend on the site that needs ablation. For example, the width of the cervical facet is only about 0.5-1.0 cm and about 1.0-2.0 cm for the lumbar facet region. Thus, the device, in various embodiments, can be designed for these specific areas.

Some examples of lengths of the probe, may include, but are not limited to, from about from about 50 to 150 mm in length, for example, about 50 mm for the cervical facet use, about 100 mm for a lumbar facet use in a standard adult and about 150 mm for an obese adult patient. The thickness of the probe will depend on the site that needs ablation and/or the particular embodiment of the device. The thickness of the probe is about 20 gauge. In some embodiments, the probe can be about 18 to about 22 gauge. In various embodiments, the thickness includes, but is not limited to, from about 0.05 to about 1.655. In some embodiments the probe can be increasing and or decreasing in thickness throughout the probe. In some embodiments, the probe may be tapered and/or angled. The probe may be the widest or smallest diameter or a diameter in between for insertion into a human or animal body. In some embodiments, the widest diameter is typically about 14 gauge, while the smallest diameter is about 26 gauge.

Probe 12 includes an interior surface 14 and an exterior surface 16 (FIG. 1). Interior surface 14 defines an internal passage 18. In some embodiments, probe 12 can have one or more passages defined by the interior surface for a pressurized material to be released into the probe as well as recirculation throughout the probe. Exterior surface 16 comprises a tip 20 positioned at a distal end of the probe.

In some embodiments, a filament 19 is disposed within the internal passage of the probe. The filament is about 0.016 inches in diameter. In some embodiments, the filament is about 0.010 to 0.015 or about 0.17 to about 0.25 inches in diameter. The filament is a conduit for cooling and expansion of the pressurized material that is released and passed into the probe.

The filament includes an opening 21 configured to release the pressurized material into the interior surface of the probe. The opening may be shaped as a regular or irregular polygon including arcuate, round, square, oblong, kidney shaped, crescent, or beveled shaped. The pressurized material is released and enters into the passage cooling and expanding within the passage via the filament.

The material is pressurized and in some embodiments, the pressure is from about 3,000 to about 6,000 pounds per square inch (PSI). In various embodiments, the material is in the form of argon, liquid nitrogen, nitric oxide, helium, air, krypton, carbon dioxide, tetrafluoromethane or xenon. When a high pressure material such as argon is used, argon will expand within the interior and will liquefy at the tip, cooling the surface of the tip. The temperature of the material is coldest at the tip of probe 12. In one embodiment, tip 20 is made of a heat conducting material such as metal so as to enable the formation of an ice ball 22. The ice ball is spherical or oval in shape.

Suitable materials that probe 12 can be made from for example are, polyurethane, polyurea, polyether(amide), PEBA, thermoplastic elastomeric olefin, copolyester, and styrenic thermoplastic elastomer, steel, aluminum, stainless steel, titanium, nitinol, tungsten, molybdenum, metal alloys with high non-ferrous metal content and a low relative proportion of iron, carbon fiber, glass fiber, plastics, ceramics or a combination thereof.

Figure 4:
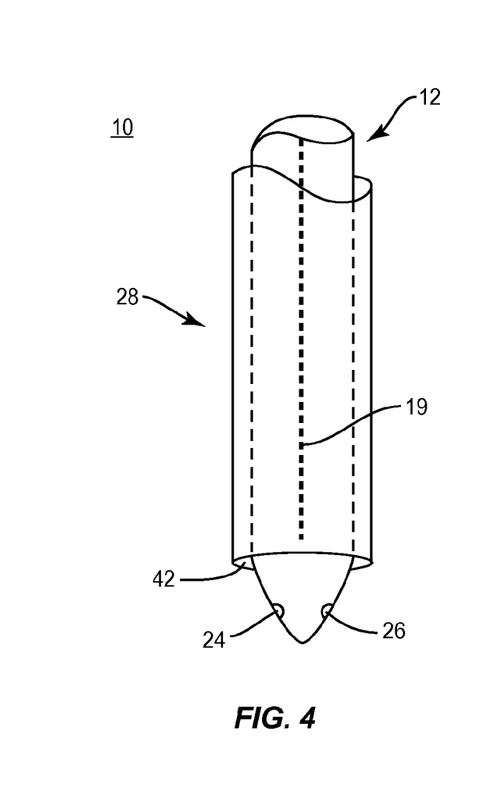
FIG. 4 illustrates a front view of an ablation device in accordance with one embodiment of the present disclosure.

In some embodiments, probe 12 has a blunt tip such that the surgeon or health practitioner can easily dispose the tip into another component of the ablation device, as described below. In some embodiments, tip 20 is pointed to allow for easy pushing through tissues (FIG. 4). In some embodiments, the tip of the probe can be round or tapered. In various embodiments, the tip is smooth for insertion.

In some embodiments, tip 20 includes openings 24, 26 respectively (FIG. 4). The openings inject pressurized material into a surgical site to facilitate an ice ball formation. The openings may be shaped as a regular or irregular polygon including arcuate, round, square, oblong, kidney shaped, crescent, or beveled shaped. In various embodiments, therapeutic agents can be delivered to the surgical site via openings 24, 26.

Device 10 includes a plurality of introducers, such as, for example, a sleeve 28 (FIGS. 1-2). In various embodiments, device 10 includes at least four sleeves (FIG. 3). In some embodiments, the sleeve is hollow. Some examples of lengths of the sleeve, may include, but are not limited to, from about 50 to about 200 mm in length depending on the surgical site and/or the size of the patient. The thickness of the sleeve will depend on the site that needs ablation and/or the particular embodiment of the device. The thickness of the sleeve is about 18 gauge. In some embodiments, the sleeve can be about 12 to about 20 gauge. In various embodiments, the thickness includes, but is not limited to, from about 0.10 to about 1.7. In some embodiments the sleeve can be increasing and or decreasing in thickness throughout the sleeve. In some embodiments, the sleeve may be tapered and/or angled. The sleeve may be the widest or smallest diameter or a diameter in between for insertion into a human or animal body. In some embodiments, the widest diameter is typically about 10 gauge, while the smallest diameter is about 22 gauge.

Sleeve 28 comprises an interior surface 30 configured for engagement with probe 12 (FIG. 1-2). Probe 12 is inserted into the interior surface of the sleeve, forming at least one air gap, such as, for example, air gaps 32, 34. The air gaps are disposed on opposing sides of exterior surface 16 of probe 12 but do not extend to the tip. The air gaps create insulation around the probe and facilitate ice ball formation at the beginning of the air gaps where the device is coldest. In some embodiments, the air gaps are symmetrical relative to one another to create a uniform ice ball or are asymmetrical relative to one another such that the ice ball can be positioned directionally. In various embodiments, the air gaps diminish or prevent collateral tissue damage at a surgical site. The air gaps, in some embodiments, will also allow directional ice ball formation. For example, if the air gap is greater on the left side of the sleeve 28, then this side will have greater insulation and thus ice ball formation will be greater on the right side, and vice versa. If the air gaps are the same, then a symmetrical ice ball will form as the insulation will be the same about the probe 12 and sleeve 28. The air gap will allow direction of the optimal temperature for cryoablation and thus the ice ball will form in that direction.

The temperature for cryoablation of the device can be selected by the user and can vary as needed. For example, the temperature that can be selected can be from −180° C., −170° C., −160° C., −150° C., −140° C., −130° C., −120° C., −110° C., −100° C., −50° C., −40° C., −30° C., −20° C., −10° C., −5° C. or to about 0° C. or any temperature in between these numbers. The device comprises an air gap between at least portions or all of the inner and outer tube to provide insulation from these temperatures.

Sleeve 28 includes an exterior surface 36 that defines an opening 38 at a proximal end. Probe 12 enters the interior surface of the sleeve via opening 38. The exterior surface comprises a heat conductive tip 40 for ablating nerve and/or soft tissue at a facet joint. The tip may comprise of a heat conductive metal such as, for example, copper, silver, gold, aluminum, brass, platinum, molybdenum and/or tungsten. Tip 40 is pointed to allow for easy pushing through tissues.

In various embodiments, the exterior surface of the sleeve defines an opening 42 at a distal end (FIG. 4). In some embodiments, tip 20 of probe 12 extends from opening 42 to ablate nerve and/or soft tissue at a facet or sacroiliac joint.

In some embodiments, tip 40 includes at least one opening such as, for example, openings 44, 46 (FIG. 2). The openings inject pressurized material into a surgical site to facilitate ice ball formation. In some embodiments, water and/or a pressurized material are released from the openings to cryoablate a surgical site. In various embodiments, therapeutic agents can be delivered to the surgical site via openings 44, 46. The openings may be shaped as a regular or irregular polygon including arcuate, round, square, oblong, kidney shaped, crescent, or beveled shaped.

In various embodiments, the probe tip is placed in contact with the sleeve tip to facilitate ablation of nerve and/or soft tissue. Probe 12 conducts temperature transfer (e.g., heat transfer) from sleeve 28 to form the ice ball at the sleeve tip up to where the air gaps between the sleeve and needle begin. In various embodiments, the tips engage in a friction fitting, clip, key/keyway clips, threaded engagement and/or male/female engagement. In some embodiments, a fluid is added to the tip of the sleeve to facilitate heat flow across any minute gap between the sleeve and the probe.

The use of sleeve 28 reduces contamination at a surgical site and allows a medical practitioner to easily remove probe 12 from the site. Because the tip of the probe is not directly in contact with an ice ball, the amount of time for a procedure is reduced. In some embodiments, positioning of tip 40 allows ablation to be applied near the tip and avoids hemisphere spacing around the tip to avoid unwanted necrosis.

In some embodiments, a lubricant is provided to assist in the insertion of tip 40 within the nerve and/or soft tissue. In some embodiments, the lubricant can be, without limitation, polyethylene glycol (PEG), hyaluronic acid, hyaluronan, lubricin, polyethylene glycol, and any combinations thereof.

After a period of time, ice ball 22 forms when the exterior surface at the tip of the sleeve contacts nerve and/or soft tissue and when the temperature at the tip decreases to about −40° C. to about −160° C. The temperature at the surface of the ice ball is 0° C. The temperature declines exponentially towards a cool center where it reaches about −170° C. The ice ball will be formed at about 2 to about 8 minutes after the material has been released into probe 12. The sphere creates a zone of complete ablation (about −20° C.) typically located within the ice ball at approximately half way between the center of the ball and its outer surface. In various embodiments, nerve and or soft tissue is completely ablated in about 3 to about 16 minutes. In various embodiments, nerve and or soft tissue is completely ablated in about 3 to about 9 minutes. In some embodiments, the ice ball is not a complete ice ball, for example, a partial or half an ice ball can be formed for complete ablation.

Figure 6:
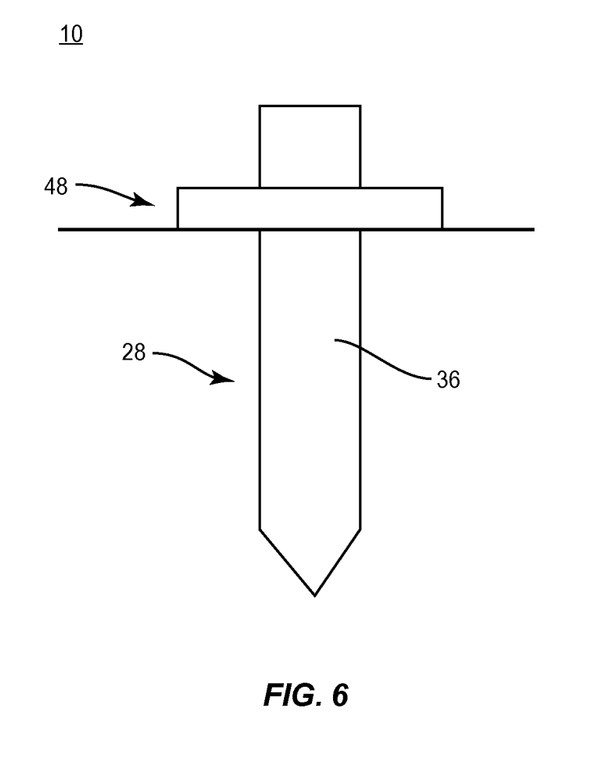
FIG. 6 illustrates a front view of an ablation device in accordance with one embodiment of the present disclosure.
Figure 7:
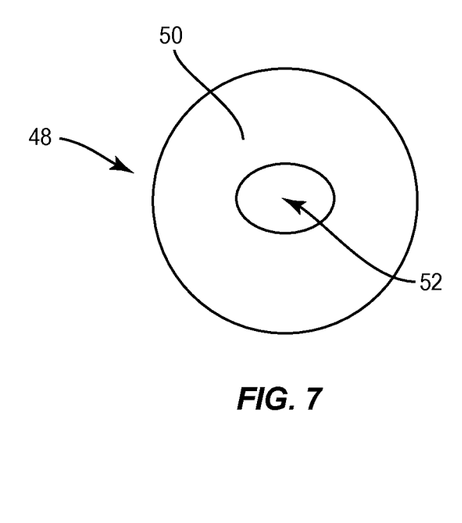
FIG. 7 illustrates a top view of an ablation device in accordance with one embodiment of the present disclosure.

Device 10 includes a stabilization disc 48 (FIGS. 6-7). The disc fixes to the exterior surface of sleeve 28 at the proximal end and engages with a part of a patient, for example the patient's skin to stabilize device 10. The disc enables the device to be positioned at a set location and prevents the device from sliding during a surgical procedure. The disc includes an exterior surface 50 that defines an opening 52. The opening fixes with the exterior surface of sleeve 28. In some embodiments, the exterior surface of the disc may be rough, arcuate, undulating, mesh, porous, semi-porous, dimpled and/or textured, or have an adhesive surface. In various embodiments, the disc fixes to the exterior surface via friction fitting, threaded engagement, adhesive or snap engagement.

In some embodiments, a heated material can pass through the internal passage of the probe to heat the pressurized material thereby increasing temperature.

In various embodiments, the device is coated with an antimicrobial coating and/or agents. The antimicrobial coating can include, for example, antibiotics, antifungal, antiviral agents or the like. Antimicrobial agents to treat infection include by way of example and not limitation, antiseptic agents, antibacterial agents; quinolones and in particular fluoroquinolones (e.g., norfloxacin, ciprofloxacin, lomefloxacin, ofloxacin, etc.), aminoglycosides (e.g., gentamicin, tobramycin, etc.), glycopeptides (e.g., vancomycin, etc.), lincosamides (e.g., clindamycin), cephalosporins (e.g., first, second, third generation) and related beta-lactams, macrolides (e.g., azithromycin, erythromycin, etc.), nitroimidazoles (e.g., metronidazole), penicillins, polymyxins, tetracyclines, or combinations thereof.

Some exemplary antimicrobial agents include, by way of illustration and not limitation, acedapsone; acetosulfone sodium; alamecin; alexidine; amdinocillin; amdinocillin pivoxil; amicycline; amifloxacin; amifloxacin mesylate; amikacin; amikacin sulfate; aminosalicylic acid; aminosalicylate sodium; amoxicillin; amphomycin; ampicillin; ampicillin sodium; apalcillin sodium; apramycin; aspartocin; astromicin sulfate; avilamycin; avoparcin; azithromycin; azlocillin; azlocillin sodium; bacampicillin hydrochloride; bacitracin; bacitracin methylene disalicylate; bacitracin zinc; bambermycins; benzoylpas calcium; berythromycin; betamicin sulfate; biapenem; biniramycin; biphenamine hydrochloride; bispyrithione magsulfex; butikacin; butirosin sulfate; capreomycin sulfate; carbadox; carbenicillin disodium; carbenicillin indanyl sodium; carbenicillin phenyl sodium; carbenicillin potassium; carumonam sodium; cefaclor; cefadroxil; cefamandole; cefamandole nafate; cefamandole sodium; cefaparole; cefatrizine; cefazaflur sodium; cefazolin; cefazolin sodium; cefbuperazone; cefdinir; cefepime; cefepime hydrochloride; cefetecol; cefixime; cefinenoxime hydrochloride; cefinetazole; cefinetazole sodium; cefonicid monosodium; cefonicid sodium; cefoperazone sodium; ceforanide; cefotaxime sodium; cefotetan; cefotetan disodium; cefotiam hydrochloride; cefoxitin; cefoxitin sodium; cefpimizole; cefpimizole sodium; cefpiramide; cefpiramide sodium; cefpirome sulfate; cefpodoxime proxetil; cefprozil; cefroxadine; cefsulodin sodium; ceftazidime; ceftibuten; ceftizoxime sodium; ceftriaxone sodium; cefuroxime; cefuroxime axetil; cefuroxime pivoxetil; cefuroxime sodium; cephacetrile sodium; cephalexin; cephalexin hydrochloride; cephaloglycin; cephaloridine; cephalothin sodium; cephapirin sodium; cephradine; cetocycline hydrochloride; cetophenicol; chloramphenicol; chloramphenicol palmitate; chloramphenicol pantothenate complex; chloramphenicol sodium succinate; chlorhexidine phosphanilate; chloroxylenol; chlortetracycline bisulfate; chlortetracycline hydrochloride; cinoxacin; ciprofloxacin; ciprofloxacin hydrochloride; cirolemycin; clarithromycin; clinafloxacin hydrochloride; clindamycin; clindamycin hydrochloride; clindamycin palmitate hydrochloride; clindamycin phosphate; clofazimine; cloxacillin benzathine; cloxacillin sodium; chlorhexidine, cloxyquin; colistimethate sodium; colistin sulfate; coumermycin; coumermycin sodium; cyclacillin; cycloserine; dalfopristin; dapsone; daptomycin; demeclocycline; demeclocycline hydrochloride; demecycline; denofungin; diaveridine; dicloxacillin; dicloxacillin sodium; dihydrostreptomycin sulfate; dipyrithione; dirithromycin; doxycycline; doxycycline calcium; doxycycline fosfatex; doxycycline hyclate; droxacin sodium; enoxacin; epicillin; epitetracycline hydrochloride; erythromycin; erythromycin acistrate; erythromycin estolate; erythromycin ethylsuccinate; erythromycin gluceptate; erythromycin lactobionate; erythromycin propionate; erythromycin stearate; ethambutol hydrochloride; ethionamide; fleroxacin; floxacillin; fludalanine; flumequine; fosfomycin; fosfomycin tromethamine; fumoxicillin; furazolium chloride; furazolium tartrate; fusidate sodium; fusidic acid; ganciclovir and ganciclovir sodium; gentamicin sulfate; gloximonam; gramicidin; haloprogin; hetacillin; hetacillin potassium; hexedine; ibafloxacin; imipenem; isoconazole; isepamicin; isoniazid; josamycin; kanamycin sulfate; kitasamycin; levofuraltadone; levopropylcillin potassium; lexithromycin; lincomycin; lincomycin hydrochloride; lomefloxacin; lomefloxacin hydrochloride; lomefloxacin mesylate; loracarbef; mafenide; meclocycline; meclocycline sulfosalicylate; megalomicin potassium phosphate; mequidox; meropenem; methacycline; methacycline hydrochloride; methenamine; methenamine hippurate; methenamine mandelate; methicillin sodium; metioprim; metronidazole hydrochloride; metronidazole phosphate; mezlocillin; mezlocillin sodium; minocycline; minocycline hydrochloride; mirincamycin hydrochloride; monensin; monensin sodium; nafcillin sodium; nalidixate sodium; nalidixic acid; natamycin; nebramycin; neomycin palmitate; neomycin sulfate; neomycin undecylenate; netilmicin sulfate; neutramycin; nifuiradene; nifuraldezone; nifuratel; nifuratrone; nifurdazil; nifurimide; nifiupirinol; nifurquinazol; nifurthiazole; nitrocycline; nitrofurantoin; nitromide; norfloxacin; novobiocin sodium; ofloxacin; onnetoprim; oxacillin and oxacillin sodium; oximonam; oximonam sodium; oxolinic acid; oxytetracycline; oxytetracycline calcium; oxytetracycline hydrochloride; paldimycin; parachlorophenol; paulomycin; pefloxacin; pefloxacin mesylate; penamecillin; penicillins such as penicillin g benzathine, penicillin g potassium, penicillin g procaine, penicillin g sodium, penicillin v, penicillin v benzathine, penicillin v hydrabamine, and penicillin v potassium; pentizidone sodium; phenyl aminosalicylate; piperacillin sodium; pirbenicillin sodium; piridicillin sodium; pirlimycin hydrochloride; pivampicillin hydrochloride; pivampicillin pamoate; pivampicillin probenate; polymyxin b sulfate; porfiromycin; propikacin; pyrazinamide; pyrithione zinc; quindecamine acetate; quinupristin; racephenicol; ramoplanin; ranimycin; relomycin; repromicin; rifabutin; rifametane; rifamexil; rifamide; rifampin; rifapentine; rifaximin; rolitetracycline; rolitetracycline nitrate; rosaramicin; rosaramicin butyrate; rosaramicin propionate; rosaramicin sodium phosphate; rosaramicin stearate; rosoxacin; roxarsone; roxithromycin; sancycline; sanfetrinem sodium; sarmoxicillin; sarpicillin; scopafungin; sisomicin; sisomicin sulfate; sparfloxacin; spectinomycin hydrochloride; spiramycin; stallimycin hydrochloride; steffimycin; streptomycin sulfate; streptonicozid; sulfabenz; sulfabenzamide; sulfacetamide; sulfacetamide sodium; sulfacytine; sulfadiazine; sulfadiazine sodium; sulfadoxine; sulfalene; sulfamerazine; sulfameter; sulfamethazine; sulfamethizole; sulfamethoxazole; sulfamonomethoxine; sulfamoxole; sulfanilate zinc; sulfanitran; sulfasalazine; sulfasomizole; sulfathiazole; sulfazamet; sulfisoxazole; sulfisoxazole acetyl; sulfisboxazole diolamine; sulfomyxin; sulopenem; sultamricillin; suncillin sodium; talampicillin hydrochloride; teicoplanin; temafloxacin hydrochloride; temocillin; tetracycline; tetracycline hydrochloride; tetracycline phosphate complex; tetroxoprim; thiamphenicol; thiphencillin potassium; ticarcillin cresyl sodium; ticarcillin disodium; ticarcillin monosodium; ticlatone; tiodonium chloride; tobramycin; tobramycin sulfate; tosufloxacin; trimethoprim; trimethoprim sulfate; trisulfapyrimidines; troleandomycin; trospectomycin sulfate; tyrothricin; vancomycin; vancomycin hydrochloride; virginiamycin; zorbamycin; or combinations thereof.

In some embodiments, the device can be coated with an antiviral agent. Antiviral agents can include, but are not limited to, vidarabine, acyclovir, famciclovir, valacyclovir, gancyclovir, valganciclovir, nucleoside-analog reverse transcriptase inhibitors (such as AZT (zidovudine), ddI (didanosine), ddC (zalcitabine), d4T (stavudine), and 3TC (lamivudine)), nevirapine, delavirdine, protease inhibitors (such as, saquinavir, ritonavir, indinavir, and nelfinavir), ribavirin, amantadine, rimantadine, neuraminidase inhibitors (such as zanamivir and oseltamivir), pleconaril, cidofovir, foscarnet, and/or interferons.

Depending on the particular embodiment, the size of the probe tip or the sleeve tip determines the size of the ice ball formed. In some embodiments, the diameter of the tips are about 0.5 to about 2 mm for smaller ice balls and from about 3 to about 6 mm for larger ice balls.

In one embodiment, sleeve 28 comprises a plurality of tips. In various embodiments, the sleeve tips can form an arcuate configuration to match a particular geometry to be ablated. For example, when positioned with a facet of a vertebra, the facet geometry is matched with the tips of the sleeve. In various embodiments, the tips are configured to match other anatomical tissue shapes to treat other painful conditions. In certain embodiments, each tip may be introduced at a specific depth to locally provide treatment to a portion of the surgical site while avoiding damage to other areas that are not intended to be ablated.

In various embodiments, the tips of device 10 comprise a telescopic configuration. The tips can be manually or electronically movable so as to place the tips into a particular position within a surgical site. In certain embodiments, all or some of the tips comprise a telescopic configuration. In some embodiments, the tip is a navigational tool used to guide device 10 into a surgical site.

In some embodiments, the tips of device 10 each comprise indicia, for example a depth indicator that may include an analog, such as, for example, a dial with a numerical indicator of angle and/or digital display, such as, for example, LED and/or LCD. The graduations may represent various indicia, such as, for example, numerical, alphabetic and/or specific conditions/orientations, such as, initial depth and/or final depth of penetration into the nerve and/or tissue.

In certain embodiments, device 10 may include switches for manually controlling the operation of device 10 by a medical practitioner. The switches can provide functions such as on/off, cooling, and predetermined cycles of heating and cooling by selectively and controllably communicating device 10 with an external material container.

In some embodiments, different monitors of temperature, gas pressure and location on device 10 can be attached to device 10. In some embodiments, thermal sensors may be used for measuring the temperature of the material and/or the tips. In some embodiments, device 10 can be operatively connected to semi-steerable or navigational sources for easier guidance into tissues. In various embodiments, the navigational sources can be coupled with a pre-procedure such as for example, CT, MRI, PET scan, etc. so that the target nerve or soft tissue to be ablated can be identified and accurately located during the procedure.

In some embodiments, device 10 is attached to a pressure source that is configured to supply the pressurized material described above. In some embodiments, without limitation, the pressure source can be a pump, a cannula and or a catheter.

In various embodiments, at a proximal end, device 10 can be operatively connected to a vacuum (not shown) for providing suction to ablated nerve and/or tissue. The vacuum may be used to transmit vacuum from a vacuum source (not shown) to a receiving aperture (not shown) connected to device 10. Any suitable aspirator, cylindrical or otherwise, or other mechanism that creates vacuum upon the movement of an actuating member thereof, may be utilized as a vacuum source. The vacuum can be in communication with the tips of device 10 for providing suction to remove ablated nerve and/or soft tissue.

With further reference to FIGS. 1-7, not shown is an overall glass or other insulating layer covering most of the structure. In some embodiments, the coating or insulating layer can be glass or ceramic having a thickness from about 0.005 to about 0.5 mm thick or from about 0.01 to about 0.2 mm thick.

The glass type insulation is typically applied by a conventional process of dipping each relevant component prior to assembly in liquid (molten) glass and then annealing the glass. In some embodiments, the coating or insulation layer does not cover the entire probe. In some embodiments, the coating or insulation layer does cover the entire probe.

In various embodiments, the device may include radiographic markers to help indicate position on imaging procedures (e.g., CT scan, X-ray, fluoroscopy, PET scan, etc.). These may be disposed on or a portion of the device and include, but are not limited to, barium, calcium phosphate, and/or metal beads.

In some embodiments, device 10 can also have blunt sleeve and/or probe tips. As a result, the surgeon or health practitioner can eliminate any difficulty in positioning the tips in the optimal location to get an optimal and consistent clinical result. The use of device 10 also results in avoiding necrosis of adjacent tissue, which can lead to clinical adverse events and requires these adjacent tissues to have to repair themselves.

Positioning of the tips allows cryoablation to be applied near the tips and avoids hemisphere spacing around the tips to avoid unwanted necrosis.

In some embodiments, the sleeve and/or probe tips can comprise grooves (not shown). Grooves can have edges shaped as a regular or irregular polygon including arcuate, round, square, oblong, oval, kidney shaped, beveled, or crescent shaped. The grooves can also include ridges or have no ridges. In various embodiments, the grooves are located at the tips and can be closed when device 10 is inactive as device 10 is inserted towards the desired location. Once the nerve or soft tissue to destroy is reached, grooves open, the material becomes activated to ablate the nerve or tissue protruding into each groove as device 10 is manually pushed into it.

In certain embodiments, device 10 can be provided with a tube or small channel (not shown) configured to deliver at the location of the severed nerve and/or soft tissue cement or polymer which can provide a physical barrier to prevent the temporary or permanent re-growth of nerve and/or soft tissue so that the pain symptoms do not return. This channel can be adjacent to the internal passage of the sleeve and can run parallel to the internal passage such that the device can ablate and deliver a therapeutic material or barrier (e.g., polymer, cement, gel, etc.) to the area after ablating it.

Methods for Ablation

Figure 5:
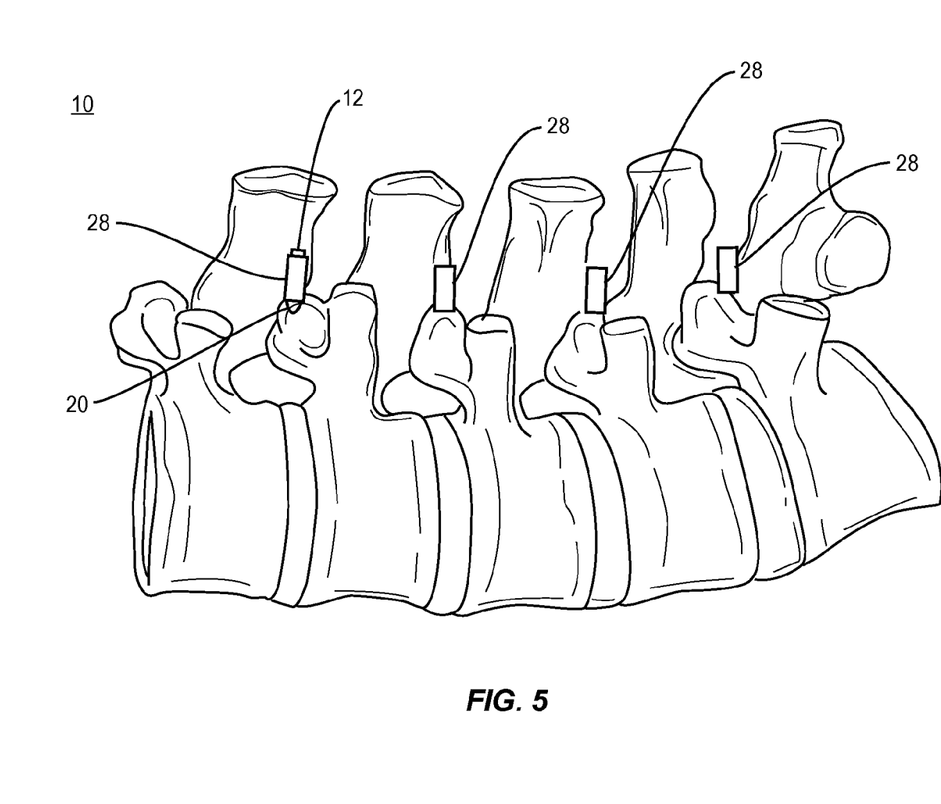
FIG. 5 illustrates a front view of an ablation device in accordance with one embodiment of the present disclosure disposed with vertebrae.

The present disclosure also provides methods for destroying or removing nerve and/or soft tissue (FIGS. 3 and 5). The methods comprise disposing a plurality of introducers at a surgical site; inserting a plurality of probes within a plurality of introducers, wherein each probe comprises an interior surface defining an internal passage and an exterior surface comprising a tip, wherein the interior surface has an opening configured to release a pressurized material into the interior surface of the probe so as to cool the exterior surface of the probe to a selected temperature and wherein each introducer comprises an interior surface configured for engagement with the probe, wherein at least one air gap is produced by the introducer and probe engagement, and an exterior surface comprising a heat conductive tip, wherein the probe tip is placed in contact with the introducer tip in a configuration for ablating nerve and/or soft tissue; and placing the device adjacent to the nerve and/or soft tissue to ablate the nerve and/or soft tissue (FIG. 3). In various embodiments, the site is a facet joint or a plurality of facets joints and the introducer tip is adjacent to the nerve and or soft tissue to form an ice ball configured for ablating the nerve and/or the soft tissue. The ice ball forms at about 2-8 minutes and the nerve is ablated in about 3-16 minutes.

In some embodiments, the user inserts a plurality of introducers at a surgical site (e.g., adjacent to the medial branch nerves) and then inserts the same or different probe into the introducer to ablate the nerve and/or target tissue site. In this way, the user saves time in the procedure. The user can ablate and move the same probe or a different probe to the next introducer and does not have to wait for the ice ball to melt using the arrangement in FIG. 3.

In various embodiments, the method comprises disposing a plurality of sleeves at a surgical site; inserting a probe into the plurality of introducers, wherein the probe comprises an interior surface defining an internal passage and an exterior surface comprising a tip, the interior surface having an opening configured to release a pressurized material into the interior surface of the probe so as to cool the exterior surface of the probe to a selected temperature and wherein each sleeve comprises an interior surface configured for disposal of the probe and an exterior surface comprising an opening, wherein the tip of the probe extends from the exterior surface opening of the sleeve to ablate nerve and/or soft tissue at a facet or sacroiliac joint; and placing the device adjacent to the nerve and/or soft tissue to ablate the nerve and/or soft tissue (FIG. 5).

In various embodiments, the site is a facet joint or a plurality of facets joints and the probe tip is adjacent to the nerve and or soft tissue to form an ice ball configured for ablating the nerve and/or the soft tissue. The ice ball forms at about 2-8 minutes and the nerve is ablated in about 3-16 minutes.

In other embodiments, the methods of the present disclosure further include delivering cement and/or a polymer through a small channel, for injection at the site of the nerve and/or soft tissue destruction to provide a physically barrier at the location of the nerve destruction to prevent temporary or permanent nerve regrowth, repair and return of the pain symptoms.

The barrier material utilized can be any suitable material effective to prevent or at least substantially inhibit the migration of substances that regrow tissue. Illustratively the barrier material can comprise a biodegradable synthetic polymer, in either flowable (and potentially hardenable) or non-flowable form. Illustratively, preferred barrier materials can have a first relatively flowable state during delivery and a second relatively less flowable state after implantation. For example, the barrier material may remain in an uncured, deformable, or otherwise configurable state during introduction, and rapidly cure, become harder or solidify after being introduced. Suitable materials that may be used for the barrier material include tissue sealants, adhesives, or implant materials made from natural or synthetic materials, including, for example, fibrin, albumin, collagen, elastin, silk and other proteins, polyethylene glycols (e.g. PEG gels), polyethylene oxide, cyanoacrylate, polylactic acid, polyglycolic acid, copolymers of polylactic acid and polyglycolic acid, polypropylene fumarate, tyrosine-based polycarbonate, ceramics, and combinations thereof. In some embodiments, the barrier material can be a cement.

In several embodiments, the methods disclosed herein include operatively coupling the device to a source of navigational capability to allow easier pushing through the tissues. In various embodiments, the methods of ablation disclosed herein can include a pre-procedure step wherein the device can be coupled to a CT or MRI machine so that the target nerve and/or soft tissue to be ablated can be identified and accurately located during the destruction procedure.

The methods for ablation described hereinabove allow complete destruction of the nerve avoiding the problems and partial effectiveness of current cryoablation and RF devices available in the art, and also allow for more complete destruction of soft tissue that is causing stenosis pain symptoms.

In various embodiments, kits are provided that include device 10. The kits can include at least one probe and at least one sleeve. In some embodiments, the probe and/or the sleeve is made reusable for multiple procedures after cleaning and sterilization.

Specific clinical application of this instrument include destruction of nerves causing facet and sacroiliac joint, and discogenic back and leg pain, destruction of soft tissue causing stenosis pain symptoms, and many other orthopedic, oral maxillofacial, and ENT pain and pathologies. Many other painful conditions associated with arthroscopic, otolaryngological or spinal procedures could use the ablation devices and methods of using these ablation devices described herein.

It will be apparent to those skilled in the art that various modifications and variations can be made to various embodiments described herein without departing from the spirit or scope of the teachings herein. Thus, it is intended that various embodiments cover other modifications and variations of various embodiments within the scope of the present teachings.

What is claimed is:

1. An ablation device comprising:
a probe comprising an interior surface defining an internal passage and an exterior surface comprising a Up, wherein the internal passage has a filament comprising an opening configured to release a pressurized material into the interior surface of the probe so as to cool the exterior surface of the probe to a selected temperature; and
an introducer comprising an exterior surface, a temperature conductive tip, and an interior surface configured for engagement with the exterior surface of the probe, wherein the ablation device comprises an air gap between at least a portion of the exterior surface of the probe and the interior surface of the introducer so as to insulate the exterior surface of the introducer from the selected temperature, and the probe tip is configured to fit within the temperature conductive tip of the introducer for ablating nerve and/or soft tissue.

2. An ablation device of claim 1, wherein (i) the probe is about a 20 gauge needle having a pointed or blunt tip and the probe comprises titanium, stainless steel, tungsten, molybdenum or alloys thereof, or (ii) the ablation device comprises a plurality of introducers configured for placement at or near the spine.

3. An ablation device of claim 1, wherein (i) the material comprises a liquid or gas comprising argon, liquid nitrogen, nitric oxide, helium, air, krypton, carbon dioxide, tetrafluoromethane or xenon, or (ii) the air gap comprises a first air gap and a second air gap disposed in a symmetrical configuration so that a symmetrical ice ball can be formed about the probe tip.

4. An ablation device of claim 1, wherein the temperature of the pressurized material decreases at or near the introducer tip and wherein the pressurized material is cooled at the introducer tip at approximately −40° to about −160° C.

5. An ablation device of claim 1, wherein the introducer is a hollow insulated sleeve that has about an 18 gauge thickness.

6. An ablation device of claim 1, wherein the exterior surface of the introducer is adjacent to the nerve and/or soft tissue at a facet or sacroiliac joint to form an ice ball configured for ablating the nerve and/or soft tissue at the facet or sacroiliac joint and wherein the air gap comprises a first air gap and a second air gap disposed in an asymmetrical configuration to form a directional ice ball.

7. An ablation device of claim 1, wherein the introducer comprises a solid metal heat conductive tip comprising copper, silver, gold, aluminum, brass, platinum, molybdenum and tungsten.

8. An ablation device of claim 1, wherein (i) the introducer comprises at least one hole at the tip to facilitate an ice ball formation via the fluid, or the at least one hole at the tip of the introducer is configured for delivery of a liquid or (ii) the probe comprises at least one hole at the tip to facilitate an ice ball formation via the fluid, or the probe comprises at least one hole configured for delivery of a liquid.

9. An ablation device of claim 8, wherein the ice ball forms at about 2-8 minutes and wherein the nerve is ablated in about 3-16 minutes.

10. An ablation device of claim 1, wherein the device includes a stabilization disc comprising an exterior surface, and an interior surface configured for a friction fit or threaded or adhesive surface with a portion of the exterior surface of the introducer and engagement with an exterior tissue of a patient's body.

11. A cryoablation device comprising:
a probe comprising an interior surface defining an internal passage and an exterior surface comprising a tip, the internal passage having a filament comprising an opening configured to release a pressurized material into the interior surface of the probe so as to cool the exterior surface of the probe to a selected temperature; and
a plurality of sleeves each of the plurality of sleeves comprising an interior surface configured to engage the probe, wherein (i) the probe tip is configured to fit within the interior surface of the sleeve for ablating nerve and/or soft tissue; or (ii) the plurality of sleeves comprise an opening configured to allow the tip of the probe to extend from the opening to ablate nerve and/or soft tissue.

12. A cryoablation device of claim 11, wherein (i) the probe is about a 20 gauge needle having a pointed or blunt tip and the probe comprises titanium, stainless steel, tungsten, molybdenum or alloys thereof; (ii) the plurality of sleeves each have only one opening for introduction of the probe; or (iii) the plurality of sleeves each have an angled tip for directional ice ball formation.

13. A cryoablation device of claim 11, wherein the material comprises a liquid or gas comprising argon, liquid nitrogen, nitric oxide, helium, air, krypton, carbon dioxide, tetrafluoromethane or xenon.

14. A cryoablation device of claim 11, wherein the temperature of the pressurized material decreases at or near the tip and wherein the pressurized material is cooled at the tip at approximately −40° to about −160° C.

15. A cryoablation device of claim 1, wherein the sleeve is hollow and has about an 18 gauge thickness.

16. A cryoablation device of claim 11, wherein the probe tip is adjacent to the nerve and/or soft tissue at a facet or sacroiliac joint to form an ice ball configured for ablating the nerve and/or soft tissue at the facet or sacroiliac joint.

17. A cryoablation device of claim 16, wherein the ice ball forms at about 2-8 minutes and wherein the nerve is ablated in about 3-16 minutes.

18. A cryoablation device of claim 11, wherein the device includes a stabilization disc comprising an exterior surface, and an interior surface configured for a friction fit or threaded or adhesive engagement with a portion of the exterior surface of the sleeve and engagement with an exterior tissue of a patient's body.

19. A method of ablating a nerve and/or soft tissue, comprising;
inserting a plurality of introducers at a surgical site;
inserting a probe within a first of the plurality of introducers, wherein each probe comprises an interior surface defining an internal passage and an exterior surface comprising a tip, the internal passage having a filament comprising an opening configured to release a pressurized material into the interior surface of the probe so as to cool the exterior surface of the probe to a selected temperature to ablate the nerve and/or soft tissue; and
removing the probe from the first of the plurality of introducers and inserting the probe into a second of the plurality of introducers to ablate the nerve and/or soft tissue adjacent to the second introducer.

20. A method of ablating a nerve and/or soft tissue of claim 19, wherein (i) the site is a facet or sacroiliac joint or a plurality of facets or sacroiliac joints and wherein the introducer tip adjacent to the nerve and or soft tissue to form an ice ball configured for ablating the nerve and/or the soft tissue; (ii) the site comprises a medial branch nerve; or (iii) the introducer comprises at least one air gap disposed in a symmetrical or asymmetrical configuration between the introducer and the probe.

* * * * *